US012703846B2

(12) United States Patent
Zhou et al.

(10) Patent No.: US 12,703,846 B2
(45) Date of Patent: Aug. 11, 2026

(54) APPARATUS AND A METHOD FOR CONTINUOUSLY HARVESTING A BIOLOGICAL SUBSTANCE PRODUCED BY A CULTURED CELL

(71) Applicant: WUXI BIOLOGICS IRELAND LIMITED, Dundalk (IE)

(72) Inventors: Weichang Zhou, Shanghai (CN); Hang Zhou, Shanghai (CN); Mingyue Fang, Shanghai (CN)

(73) Assignee: WUXI BIOLOGICS IRELAND LIMITED, Dundalk (IE)

( * ) Notice: Subject to any disclaimer, the term of this patent is extended or adjusted under 35 U.S.C. 154(b) by 923 days.

(21) Appl. No.: 17/792,128

(22) PCT Filed: Jan. 13, 2021

(86) PCT No.: PCT/CN2021/071364

§ 371 (c)(1),
(2) Date: Jul. 11, 2022

(87) PCT Pub. No.: WO2021/143699

PCT Pub. Date: Jul. 22, 2021

(65) Prior Publication Data

US 2023/0047549 A1 Feb. 16, 2023

(30) Foreign Application Priority Data

Jan. 15, 2020 (WO) ................ PCT/CN2020/072216

(51) Int. Cl.
*C12M 1/00* (2006.01)
*C07K 14/505* (2006.01)

(52) U.S. Cl.
CPC .......... *C12M 47/10* (2013.01); *C07K 14/505* (2013.01); *C12M 29/04* (2013.01); *C12M 29/10* (2013.01)

(58) Field of Classification Search
None
See application file for complete search history.

(56) References Cited

U.S. PATENT DOCUMENTS 5,166,067 A 11/1992 Ishida et al.
9,428,724 B2 8/2016 Fricking
2004/0259240 A1 12/2004 Fadden
(Continued)

FOREIGN PATENT DOCUMENTS

CN 101503707 A 8/2009
CN 103080300 5/2013
(Continued)

OTHER PUBLICATIONS

English translation of Chinese Office Action dated Apr. 3, 2024 regarding CN Application No. 202180010027, 5 pages.
(Continued)

*Primary Examiner* — William H. Beisner
(74) *Attorney, Agent, or Firm* — James S. Keddie; Bozicevic, Field & Francis LLP

(57) ABSTRACT

An apparatus and a method for continuously harvesting a biological substance produced by a cultured cell. An apparatus and a method for continuously harvesting a biological substance produced by a cultured cell using 2 sets of filters having different pore sizes.

23 Claims, 7 Drawing Sheets

(56) References Cited

U.S. PATENT DOCUMENTS

| | | | | |
|---|---|---|---|---|
| 2010/0184149 | A1* | 7/2010 | Laustsen | C12P 21/02 435/71.1 |
| 2010/0184197 | A1 | 7/2010 | Dong et al. | |
| 2015/0118745 | A1 | 4/2015 | Iwamoto et al. | |
| 2017/0067010 | A1 | 3/2017 | Laustsen | |
| 2017/0114381 | A1 | 4/2017 | Goudar et al. | |
| 2018/0057783 | A1 | 3/2018 | Paldus et al. | |
| 2018/0148677 | A1 | 5/2018 | Kudugunti et al. | |
| 2019/0153381 | A1* | 5/2019 | Angelini | C12M 29/04 |
| 2019/0169559 | A1 | 6/2019 | Coffman et al. | |
| 2019/0264154 | A1 | 8/2019 | Laustsen | |
| 2019/0322975 | A1 | 10/2019 | Nakai et al. | |
| 2020/0063106 | A1 | 2/2020 | Shibuya et al. | |

FOREIGN PATENT DOCUMENTS

| | | | |
|---|---|---|---|
| CN | 106687575 | A | 5/2017 |
| CN | 108424851 | A | 8/2018 |
| CN | 109072154 | A | 12/2018 |
| CN | 109689191 | A | 4/2019 |
| CN | 109983116 | A | 7/2019 |
| CN | 110268043 | A | 9/2019 |
| EP | 3360955 | A1 | 8/2018 |
| JP | H0265778 | A | 3/1990 |
| JP | H02150272 | A | 6/1990 |
| JP | H06237754 | A | 8/1994 |
| JP | 2006527642 | A | 12/2006 |
| JP | 2017511144 | A | 4/2017 |
| JP | 2019126341 | A | 8/2019 |
| TW | 201400613 | A | 1/2014 |
| WO | WO 2018/003476 | A1 | 1/2018 |
| WO | WO 2018/159847 | A1 | 9/2018 |
| WO | WO2019079188 | | 4/2019 |
| WO | WO 2020/066987 | A1 | 4/2020 |

OTHER PUBLICATIONS

English translation of Search Report regarding CN Application No. 202180010027, 2 pages.

EP Search Report dated Apr. 26, 2024 regarding EP application No. EP21741942, 9 pages.

* cited by examiner

APPARATUS AND A METHOD FOR CONTINUOUSLY HARVESTING A BIOLOGICAL SUBSTANCE PRODUCED BY A CULTURED CELL

CROSS-REFERENCE TO RELATED APPLICATION

The present application is a § 371 national phase of International Application No. PCT/CN2021/071364, filed on Jan. 13, 2021, which claims the benefits of PCT Application No. PCT/CN2020/072216 filed on Jan. 15, 2020, which applications are incorporated by reference herein.

FIELD

The present disclosure relates to an apparatus and a method for continuously harvesting a biological substance produced by a cultured cell. More particularly, the present disclosure relates to an apparatus and a method for continuously harvesting a biological substance produced by a cultured cell using 2 sets of filters having different pore sizes.

BACKGROUND

Traditional perfusion culture (TPC) and intensified perfusion culture (IPC) require continuous perfusion of fresh medium (feed medium) to the culture system to maintain growth of cells and production of biological substance. However, because the harvest rate and perfusion rate are usually equal, the target product concentration in the harvest solution is low and the harvest volume is large, which render burden to downstream purification, and require tanks of large size to store the harvest cell culture fluid, leading to an inflated cost of equipment and land. Moreover, long-term and high-flow harvesting operation can easily cause clogging of a hollow fiber filter, which will cause the target product to be retained in the culture system, while replacement of the hollow fiber filter will increase production costs, operational complexity and contamination risks.

Therefore, in order to solve the problems existing in the above-mentioned prior art culture processes, the present inventor had developed a new apparatus and a new method for continuously harvesting a biological substance produced by a cultured cell, which are applicable to production of both stable and unstable biological substances of interests.

SUMMARY

In one aspect, the present disclosure provides an apparatus for continuously harvesting a biological substance produced by a cultured cell (referred to also as "the apparatus of the present disclosure" herein below), wherein the apparatus comprises:

(a) filter 1 which is at least one filter(s) having pore size(s) which do(es) not allow the cell to pass through the filter, but allow the biological substance to pass through the filter, and (b) filter 2 which is at least one filter(s) having pore size(s) which do(es) not allow both the cell and the biological substance to pass through the filter, but keep fluid-flow-through of the filter, wherein the filter 1 and the filter 2 are fluidly connected to an apparatus for culturing the cell in a parallel manner.

In one embodiment of the apparatus of the present disclosure, the filter 1 and the filter 2 are fluidly connected to the apparatus for culturing the cell (a) directly and separately, (b) via a branched pipe, or (c) a combination of (a) and (b).

In some embodiments of the apparatus of the present disclosure, the filter 1 has a pore size of about 0.08 μm to 0.5 μm, preferably about 0.1 μm to 0.4 μm, more preferably about 0.2 μm. In some embodiments of the apparatus of the present disclosure, the filter 2 has a molecular weight cut-off (MWCO) of 50 kD or less.

In some embodiments of the apparatus of the present disclosure, the apparatus of the present disclosure further comprises a device for regulating filtering rate of the filter 1 and/or a device for regulating filtering rate of the filter 2.

In some embodiments of the apparatus of the present disclosure, either or both of the filter 1 and the filter 2 is/are alternating tangential flow (ATF) filter(s) or tangential flow filtration (TFF) filter(s). In a further embodiment of the apparatus of the present disclosure, either or both of the filter 1 and the filter 2 is/are hollow fiber filter(s).

In some embodiments of the apparatus of the present disclosure, the number of the filter 1 is 1, 2, 3 or more, and/or the number of the filter 2 is 1, 2, 3 or more.

In another aspect, the present disclosure provides system for producing a biological substance (referred to also as "the system of the present disclosure" herein below), wherein the system comprises:

(a) an apparatus for culturing a cell with a basal medium and a feed medium in a perfusion manner; and (b) the apparatus of the present disclosure.

In some embodiments of the system of the present disclosure, the system further comprises an apparatus for continuously capturing the biological substance from the materials harvested by the apparatus of the present disclosure.

In some embodiments of the system of the present disclosure, the system further comprises a microsparger.

In another aspect, the present disclosure provides a method for continuously harvesting a biological substance produced by a cultured cell, which is carried out by the apparatus of the present disclosure. In further aspect, the present disclosure provides a method for producing a biological substance, which is carried out by the system of the present disclosure. Both the methods as mentioned above are referred to also as "the method of the present disclosure" herein below.

In some embodiments of the method of the present disclosure, the cells comprise mammalian cells. In one embodiment, the mammalian cells comprise CHO (Chinese Hamster Ovary) cells, hybridomas, BHK (Baby Hamster Kidney) cells, or myeloma cells.

In some embodiments of the method of the present disclosure, the biological substance is chosen from receptors, enzymes, fusion proteins, blood proteins, multifunctional proteins, viral or bacterial proteins, and immunoglobulins. In one embodiment of the method of the present disclosure, the blood proteins are from the blood coagulation cascade. In one embodiment of the method of the present disclosure, the multifunctional proteins are erythropoietin. In one embodiment of the method of the present disclosure, the viral or bacterial proteins are used in vaccines. In one embodiment of the method of the present disclosure, the immunoglobulins are antibodies or multi-specific antibodies. In one embodiment of the method of the present disclosure, the antibodies are IgG or IgM. In one embodiment of the method of the present disclosure, the multi-specific antibodies are bi-specific antibodies.

DETAILED DESCRIPTION

I. Definitions

Figure 1A:
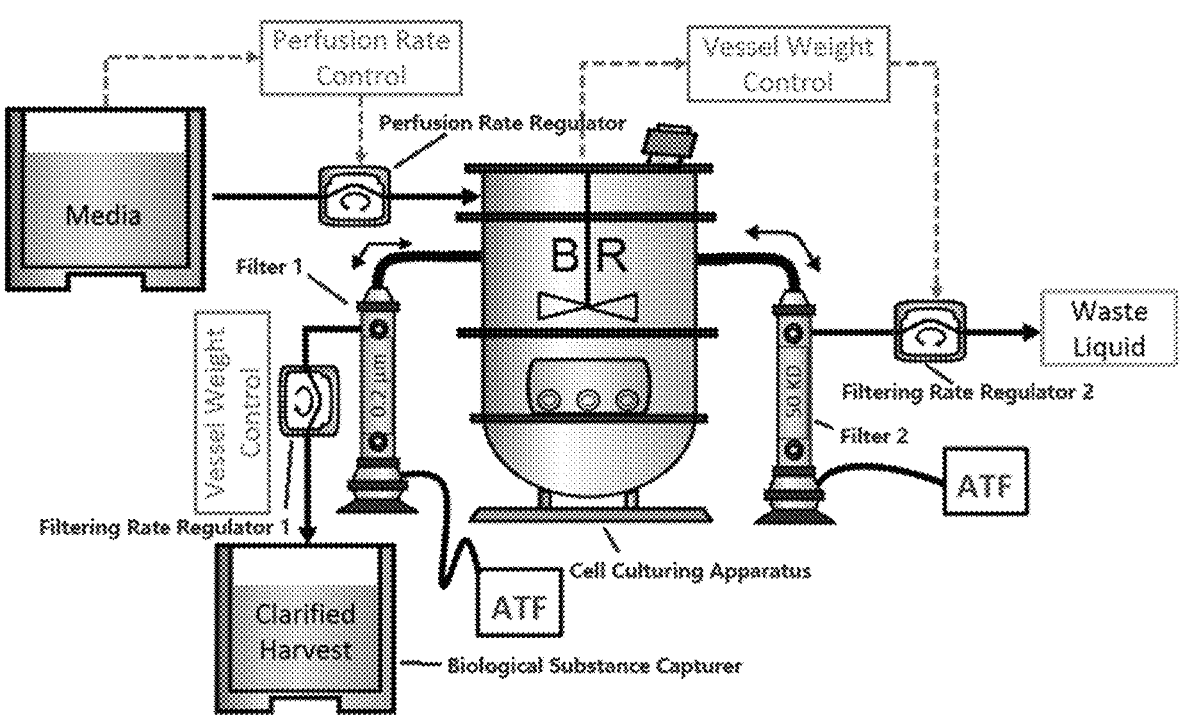
FIG. 1*a* is a schematic diagram of a culture system according to at least one embodiment of the present disclosure.
Figure 1B:
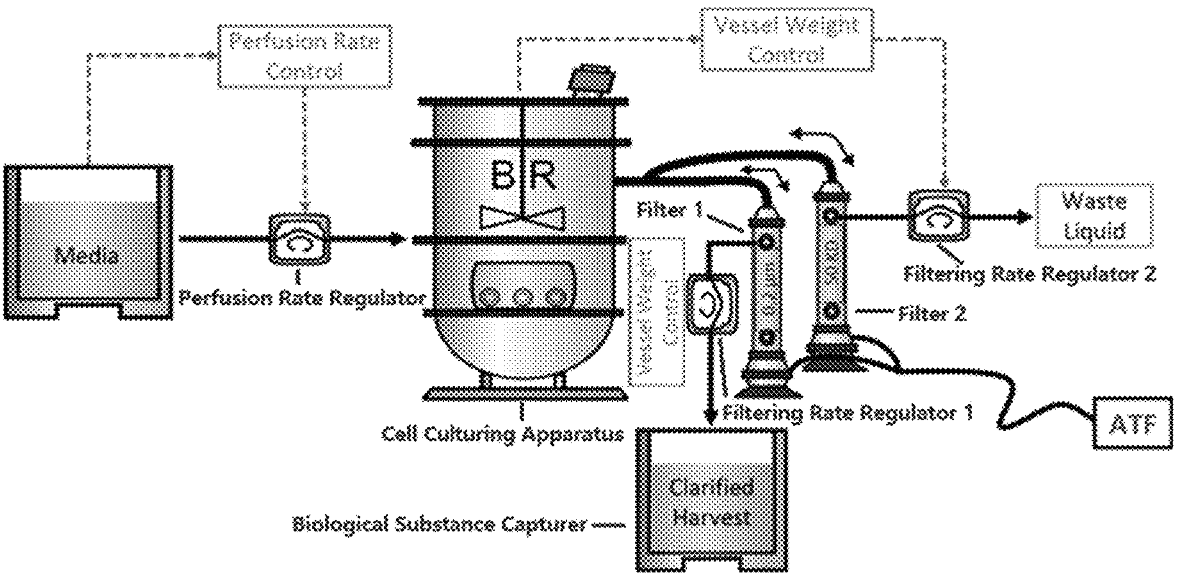
FIG. 1*b* is a schematic diagram of a culture system according to at least one embodiment of the present disclosure.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" biological substance includes one or more biological substances.

A "bioreactor" as used herein is a system that can comprise a cell culture which cell culture on its turn comprises cells and a cell culture medium. In some embodiments, it provides sterile barriers, such as air filters, to prevent other cells from contaminating the desired cells. In some embodiments, it maintains a favorable environment for the cells by providing the suitable culture conditions such as mixing, temperature, pH, oxygen concentration etc.

By "cell culture" or "culture" is meant the growth and propagation of cells outside of a multicellular organism or tissue. "Cell culture" includes the liquid comprising a cell culture medium, cells and a biological substance, which liquid is the result of a process for the culturing of cells in a reactor in a cell culture medium, wherein the cells produce the biological substance. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate.

By "cells" is meant cells that produce a biological substance of interest, for instance cells capable of expressing a gene encoding the product. Cells capable of expressing a gene encoding the product may for example be prepared by transfection of the cells with a plasmid containing the gene encoding the cell product and gene encoding a suitable selection marker. Cells which can be used to produce the product are in principle all cells known to the person skilled in the art, which have the ability to produce a biological product. The cells may be animal cells, in particular mammalian cells. Examples of mammalian cells include CHO (Chinese Hamster Ovary) cells, hybridomas, BHK (Baby Hamster Kidney) cells, myeloma cells, human cells, for example HEK-293 cells, human lymphoblastoid cells, E1 immortalized HER cells, mouse cells, for example NSO cells.

As used herein, the term "cell culturing medium" (also called "culture medium" "cell culture media") refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range.

A "basal cell culture medium" refers to a cell culture medium that is typically used to initiate a cell culture and is sufficiently complete to support the cell culture. Commercially available basal medium can be utilized and include, but is not limited to CD OptiCHO AGT (Invitrogen), CD CHO AGT (Invitrogen), Dynamis AGT Medium (Invitrogen), SFM4CHO ADCF (Hyclone), HyCell CHO Medium (Hyclone), CDM4MAB (Hyclone), DPM Hyclone ActiPro (Hyclone), Advanced CHO Fed-batch Medium (Sigma).

A "feed" cell culture medium or feed medium refers to a cell culture medium that is typically used in cell cultures during a period of exponential growth, a "growth phase", and is sufficiently complete to support the cell culture during this phase. A growth cell culture medium may also contain one or more selection agents that confer resistance or survival to selectable markers incorporated into the host cell line. Such selection agents include, but are not limited to, geneticin (G4118), neomycin, hygromycin B, puromycin, zeocin, methionine sulfoximine, methotrexate, glutamine-free cell culture medium, cell culture medium lacking glycine, hypoxanthine and thymidine, or thymidine alone. Commercially available feed medium can be utilized and include, but is not limited to CHO CD Efficient FeedA (Invitrogen), CHO CD Efficient FeedB (Invitrogen), CHO CD Efficient FeedC (Invitrogen), Sheff-CHO PLUS PF ACF(FM012) (Kerry), CHO CD Efficient Feed A+(Invitrogen), CHO CD Efficient Feed B+(Invitrogen), CHO CD Efficient Feed C+(Invitrogen), DPM-Cell Boost 7a (Hyclone), DPM-Cell Boost 7b (Hyclone), or FAA01A (Hyclone).

Cell culture medium, in certain embodiments, is serum-free and/or free of products or ingredients of animal origin. Cell culture medium, in certain embodiments, is chemically defined, where all of the chemical components are known. Commercially available media can be utilized and supplementary components or ingredients, including optional components, in appropriate concentrations or amounts, as necessary or desired, can be added, as would be known and practiced by those having in the art using routine skill.

In the context of the present disclosure, the terms "product," "biologic" and "biological substance" are interchangeable. Products, which may be produced by the cells, for example by expressing a (recombinant) gene coding therefore are for example (recombinant) proteins, in particular receptors, enzymes, fusion proteins, blood proteins such as proteins from the blood coagulation cascade, multifunctional proteins such as for instance erythropoietin, virus or bacterial proteins for instance for use in vaccines; immunoglobulins such as antibodies, for example IgG or IgM, multi-specific antibodies such as bi-specific antibodies and the like. Preferably a protein, more preferably an antibody is produced by the cells.

The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')2, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883), VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor Vila-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the disclosure include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizomab, zalutumumab, and zanolimumab.

In some embodiments, the products such as proteins or vaccines produced by the cells can be used as an active ingredient in a pharmaceutical preparation. Non-limiting examples of products includes: anti-hTNFα (Adalimumab (Humira™)), a fusion protein targeting VEGF (Aflibercept (EYLEA™)), erythropoietin alpha (Epogen®), lymphoblastoid Interferon α-n1 (Wellferon™) (recombinant) Coagulation factor (NovoSeven™), Etanercept (Enbrel™), Trastuzumab (Herceptin™), Infliximab (Remicade™), Basiliximab (Simulect™), Daclizumab (Zenapaz™) (recombinant) Coagulation factor IX (Benefix™), Glucocerebrosidase (Cerezyme™), Interferon beta 1b (Betaseron®), G-CSF (Neupogen®Filgrastim), Interferon alpha-2b (Infergen®), recombinant insulin (Humulin®), Interferon beta 1 a (Avonex®), Factor VIII (KoGENate®), Tenecteplase (TNKase™), (recombinant) antihemophilic factor (ReFacto™), TNF alpha receptor (Enbrel®), Follicle stimulating hormone (Gonal-F®), Mab abcixmab (Synagis®, ReoPro®), Mab ritiximab (Rituxan®), tissue plasminogen activator (Activase®, Actilyase®), human growth hormone (Protropin®, Norditropin®, GenoTropin™). Furthermore, the definition of the term "antibody construct" includes monovalent, bivalent and polyvalent/multivalent constructs and, thus, bispecific constructs, specifically binding to only two antigenic structure, as well as polyspecific/multispecific constructs, which specifically bind more than two antigenic structures, e.g. three, four or more, through distinct binding domains. Moreover, the definition of the term "antibody construct" includes molecules consisting of only one polypeptide chain as well as molecules consisting of more than one polypeptide chain, which chains can be either identical (homodimers, homotrimers or homo oligomers) or different (heterodimer, heterotrimer or heterooligomer). Examples for the above identified antibodies and variants or derivatives thereof are described inter alia in Harlow and Lane, Antibodies a laboratory manual, CSHL Press (1988) and Using Antibodies: a laboratory manual, CSHL Press (1999), Kontermann and Dubel, Antibody Engineering, Springer, 2nd ed. 2010 and Little, Recombinant Antibodies for Immunotherapy, Cambridge University Press 2009.

As used herein, the term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the disclosure may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

The term "microsparger" generally refers to a sparger configured to provide oxygen and/or other gases to a cell culture within a bioreactor tank. An aerator or microsparger may be coupled to a source of oxygen or other gas, and may direct the gas to the cell culture so that the gas bubbles in the cell culture, thereby aerating the cell culture. In some examples, a microsparger may be used in combination with a drilled tube sparger.

Biologics prepared as described herein may be purified by art-known techniques such as high-performance liquid chromatography, ion exchange chromatography, gel electrophoresis, affinity chromatography, size exclusion chromatography (SEC), and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the biologic binds. For example, for affinity chromatography purification of a biologic (e.g., immunoconjugates) of the disclosure, a matrix with protein A or protein G may be used. Sequential Protein A or G affinity chromatography and size exclusion chromatography can be used to isolate a biologic, e.g., an immunoconjugate, e.g., as described in the Examples. The purity of the biologic (e.g., immuno-conjugate) can be determined by any of a variety of well-known analytical methods including gel electrophoresis, high pressure liquid chromatography, and similar methods.

In the present disclosure, the term "harvest rate" means a rate that the culture product passing through the filter 1 which is at least one filter(s) having pore size(s) which do(es) not allow the cell to pass through the filter, but allow the biological substance to pass through the filter.

II. An Apparatus and a Method for Continuously Harvesting a Biological Substance Produced by a Cultured Cell In various embodiments, the biological substance produced by a cultured cell is continuously harvested by the apparatus of the present disclosure. Any kind of filter may be used as the apparatus of the present disclosure, as long as one set of filter(s) (e.g. filter 1) have/has pore size(s) which do(es) not allow the cell to pass through the filter, but allow the biological substance to pass through the filter, and the other set of filter(s) (e.g. filter 2) have/has pore size(s) which do(es) not allow both the cell and the biological substance to pass through the filter, but keep fluid-flow-through of the filter, wherein the filter 1 and the filter 2 are fluidly connected to an apparatus for culturing the cell in a parallel manner. In one embodiment of the apparatus of the present disclosure, the filter 1 and the filter 2 are fluidly connected to the apparatus for culturing the cell (a) directly and separately, (b) via a branched pipe, or (c) a combination of (a) and (b). In some embodiments of the apparatus of the present disclosure, the filter 1 has a pore size of about 0.08 μm to 0.5 μm, preferably about 0.1 μm to 0.4 μm, more preferably about 0.2 μm. In some embodiments of the apparatus of the present disclosure, the filter 2 has a molecular weight cut-off (MWCO) of 50 kD or less, 45 kD or less, 40 kD or less, 35 kD or less, 30 kD or less, 25 kD or less, 20 kD or less, etc. Approximate correspondences between pore sizes in diameter (μm) and cutoffs (kD) are as follows.

| Pore size in diameter (μm) | 0.001 | 0.002 | 0.003 | 0.004 | 0.005 | 0.006 | 0.007 | 0.008 | 0.01 | 0.05 | 0.12 | 0.2 |
|---|---|---|---|---|---|---|---|---|---|---|---|---|
| Pore size in cutoff (kD) | 1 | 3 | 5 | 6 | 10 | 20 | 30 | 50 | 100 | 150 | 300 | 500 |

Benefit from the diversion effect of filter 2, the flow rate through the filter 1 can be reduced, and thus the risk of clogging of filter 1 can be effectively reduced or avoided, thereby extending service life of the filter 1.

Since a part of waste liquid in the harvest is removed through the filter 2, the volume of harvest liquid can be reduced effectively, thereby reducing the volume and storage space of storage equipment effectively.

Since a part of waste liquid in the harvest is removed through the filter 2, target biological substance harvested can be effectively concentrated, which can effectively reduce burden of downstream purification.

Since some small molecular biological substances which are beneficial for maintaining cell viability (such as PF68)

can be remained in the culture system by the filter 2, viable cell density (VCD) in the culture system can be increased, thereby extending the culture period, and increasing batch yield.

In some embodiments of the apparatus of the present disclosure, the apparatus of the present disclosure further comprises a device for regulating filtering rate of the filter 1 and/or a device for regulating filtering rate of the filter 2. Benefit from such device(s), the ratio of flow rate of the cell culture through the filter 1 and filter 2 can be regulated as required, such that the biological substance in the harvest liquid can be concentrated to a desired extent.

The circulation of the cell culture over a filter is a flow substantially parallel to the filter surface, also known as tangential flow, for example unidirectional tangential flow filtration (TFF) or cross-flow. A preferred example of cross-flow is alternating tangential flow (ATF) as with ATF it was found that filter clogging does not occur (quickly) even at very high cell densities. With "alternating tangential flow" is meant that there is one flow in the same direction as (i.e. tangential to) the filter surface(s), which flow is going back and forth, and that there is another flow in a direction substantially perpendicular to said filter surface. Alternating tangential flow can be achieved according to methods known to a person skilled in the art (for example as described to U.S. Pat. No. 6,544,424 which is incorporated herein by reference in its entirety).

Non-limiting examples of filters suitable for use in the present disclosure include membrane filters, ceramic filters and metal filters. The filter may be used in any shape; the filer may for example be spiral wound or tubular or may be used in the form of a sheet. In various embodiments, the filter used is a membrane filter. In at least one embodiment, the filter is a hollow fiber filter. Filter apparatuses comprising hollow fibers are commercially available from, for example, Refine Technology.

In some embodiments of the apparatus of the present disclosure, the number of the filter 1 is 1, 2, 3 or more, and/or the number of the filter 2 is 1, 2, 3 or more.

In another aspect, the present disclosure provides a method for continuously harvesting a biological substance produced by a cultured cell, which is carried out by the apparatus of the present disclosure as described above.

III. A System and a Method for Producing a Biological Substance

The present disclosure provides system for producing a biological substance which comprises:

(a) an apparatus for culturing a cell with a basal medium and a feed medium in a perfusion manner; and
(b) the apparatus of the present disclosure as described above.

A "perfusion" culturing process is one in which the cell culture receives the addition of fresh medium and spent medium is removed from the bioreactor. Perfusions can be continuous, stepwise, intermittent, or a combination of any or all of any of these.

In various embodiments, a cell culture is established by inoculating cells expressing a biological substance of interest in a bioreactor. The cell culture is maintained by feeding the basal medium and a feed medium.

The rate of addition of cell culture medium to the culture may influence the viability and the density of the cells. The term "viable cell density (VCD)" refers to the number of live cells in a given volume of culture medium, as determined by standard viability assays (such as trypan blue dye exclusion method).

In at least one embodiment of the present disclosure, a microsparger is used in the method of the present disclosure. In further embodiment of the present disclosure, the microsparger is used when demanded oxygen flow rate reaches about 0.5 VVM. In the present disclosure, the implement of microsparger alleviates cell damage caused by bubbles burst during culture.

In another aspect, the present disclosure provides a method for producing a biological substance, which is carried out by the system of the present disclosure as described above.

EXAMPLES

The present disclosure, thus generally described, will be understood more readily by reference to the following Examples, which are provided by way of illustration and are not intended to be limiting of the present disclosure.

Cell Line and Culture Condition

CHO-K1 host cell was purchased from ATCC (ATCC No.: CCL 61), and the vial was thawed and 100 vials of a master cell bank (MCB) were generated followed by generation of 136 vials of a working cell bank (WCB). Then the WCB vial was thawed and adapted into suspension culture with serum free media. 60 vials of PCB, 170 vials of MCB and 230 vials of WCB were generated with the suspension adapted clone CHO-K1-A4. One WCB vial of the CHO-K1 host cell CHO-K1-A4) was thawed for stable transfection.

The cDNA sequence for expressing an anti-hTNFα antibody as disclosed in U.S. Pat. No. 6,090,382 was cloned into two vectors, which contained Blasticidin and Zeocin resistance markers, respectively. Stable transfection was performed using liposome. After transfection, cells were passaged in selective media (CD CHO media containing 9 μg/mL Blasticidin and 400 μg/mL Zeocin) for pool selection. After about 2 weeks of pool selection, the pools were cloned by FACS sorting. The clones were screened by fed-batch cultures in spin tubes. One high-producing clone, named Clone X, was selected.

Example 1

In this example, using Clone X, the performance of the intensified perfusion culture (IPC) processes carried out with the apparatus and method of the present disclosure but with different harvest rates (Process-1 and Process-2) were evaluated.

Process-1

Process-1 was performed in a 7 L Applikon vessel using delta V controller to control temperature at 36.5° C., a pH range of about between 7.2 and 6.8 and DO at 40% air saturation. A 0.2 μm cut-off hollow fiber filter (a filter 1) (Spectrum labs) operated in ATF flow mode with an ATF-2H system (Refine Technology) was used to retain the cells. A 50 kD (about 0.008 μm) cut-off hollow fiber filter (filter 2) (Spectrum labs) operated in ATF flow mode with an ATF-2H system (Refine Technology) was used to retain both cells and recombinant protein. The filter 1 and the filter 2 were fluidly connected to the Applikon vessel in a parallel manner via a branched pipe.

The culture was started with an initial VCD of 0.90-1.10×$10^6$ cells/mL in Excell Advanced CHO Fed-batch medium (Sigma) supplemented with 6.0 mM L-Glutamine. About 10 to 100 ppm antifoam was added every day from Day 0.

Perfusion of basal medium (Excell Advanced CHO Fed-batch medium, Sigma) was started from Day 1 at a rate of 0.4 WD and was increased to 1.5 VVD on Day 3. Perfusion of feed medium (CB7a/CB7b) was started from Day 4 and its rate was adjusted daily to sustain a minimum glucose concentration above 2.0 g/L. From Day 3 till the terminal of culture, the perfusion rate was kept at 1.5 VVD. Use microsparger when the demanded oxygen flow rate reached 0.5 VVM. Temperature was shifted from 36.5° C. to 31.0° C. on Day 5 and kept at 31.0° C. until culture termination.

To perform a condensed continuous harvest, the filtrate through filter 1 with recombinant protein, namely the harvest, was continuously collected. Meanwhile, the filtrate through filter 2 without recombinant protein was discarded to keep a constant working volume. The harvest rate was equal to the perfusion rate before Day 13 and was decreased to one third of the perfusion rate after Day 13. During the whole culture process, cells were retained in the bioreactor without bleeding.

Process-2

Process-2 was performed in a 7 L Applikon vessel using delta V controller to control temperature at 36.5° C., a pH range of about between 7.2 and 6.8 and DO at 40% air saturation. A 0.2 μm cut-off hollow fiber filter (a filter 1) (Spectrum labs) operated in ATF flow mode with an ATF-2H system (Refine Technology) was used to retain the cells. A 50 kD (about 0.008 μm) cut-off hollow fiber filter (filter 2) (Spectrum labs) operated in ATF flow mode with an ATF-2H system (Refine Technology) was used to retain both cells and recombinant protein. The filter 1 and the filter 2 were fluidly connected to the Applikon vessel in a parallel manner via a branched pipe.

The culture was started with an initial VCD of 0.90-1.10×$10^6$ cells/mL in Excell Advanced CHO Fed-batch medium (Sigma) supplemented with 6.0 mM L-Glutamine. About 10 to 100 ppm antifoam was added every day from Day 0. Perfusion of basal medium (Excell Advanced CHO Fed-batch medium, Sigma) was started from Day 1 at a rate of 0.4 WD and was increased to 1.5 VVD on Day 3. Perfusion of feed medium (CB7a/CB7b) was started from Day 4 and its rate was adjusted daily to sustain a minimum glucose concentration above 2.0 g/L. From Day 3 till the terminal of culture, the perfusion rate was kept at 1.5 VVD. Use microsparger when the demanded oxygen flow rate reached 0.5 VVM. Temperature was shifted from 36.5° C. to 31.0° C. on Day 5 and kept at 31.0° C. until culture termination.

To perform a condensed continuous harvest, the filtrate through filter 1 with recombinant protein, namely the harvest, was continuously collected. Meanwhile, the filtrate through filter 2 without recombinant protein was discarded to keep a constant working volume. The harvest rate was one third of the perfusion rate before Day 13 and was equal to the perfusion rate from Day 13 to Day 17, and was then decreased to one third of the perfusion rate after Day 17. During the whole culture process, cells were retained in the bioreactor without bleeding.

Comparison Between the Process-1 and the Process-2

Figure 2:
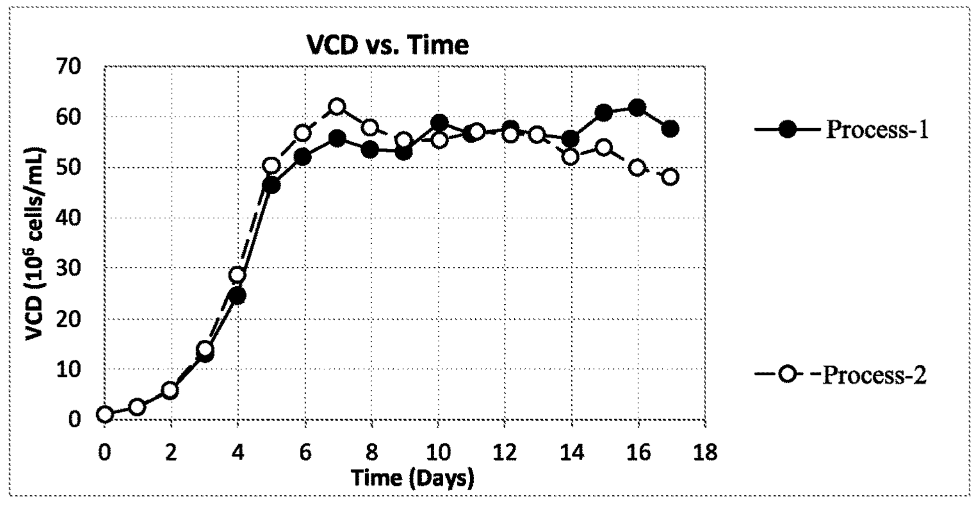
FIG. 2 showed the viable cell density ($10^6$/mL) plotted versus the process time (days) for Process-1 and Process-2.

FIG. 2 showed that a higher peak viable cell density was achieved in the process with condensed harvest (in Process-1 after Day 13, and in Process-2 before Day 13).

Figure 3:
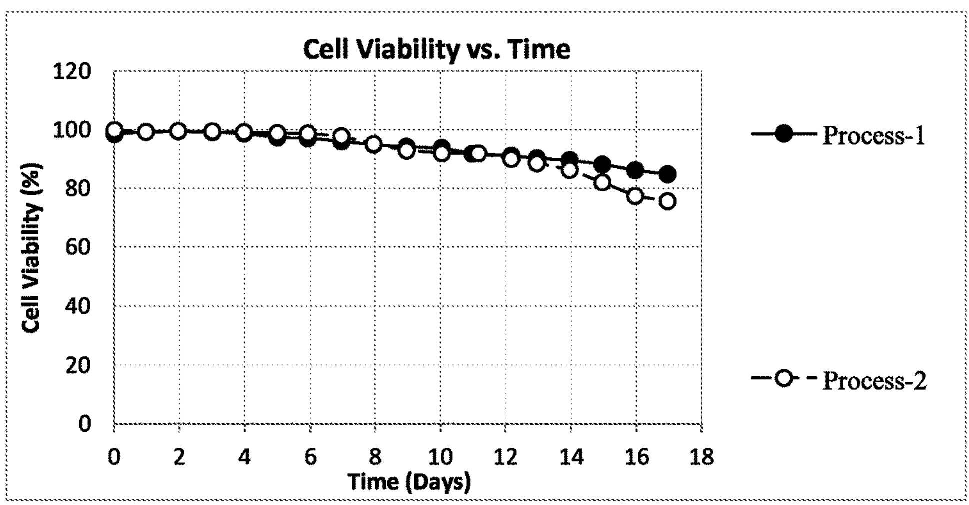
FIG. 3 showed the cell viability (%) plotted versus the process time (days) for Process-1 and Process-2.

FIG. 3 showed that the viability of cells was maintained higher in the process with condensed harvest (in Process-1 after Day 13, and in Process-2 before Day 13).

Figure 4:
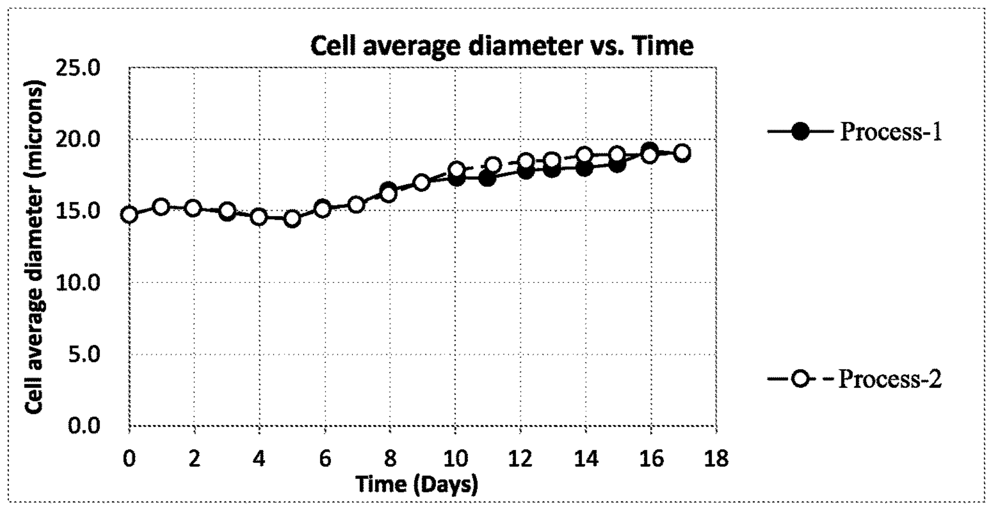
FIG. 4 showed the cell average diameter (μm) plotted versus the process time (days) for Process-1 and Process-2.

FIG. 4 showed that cell average diameters in Process-1 and Process-2 were comparable.

Figure 5:
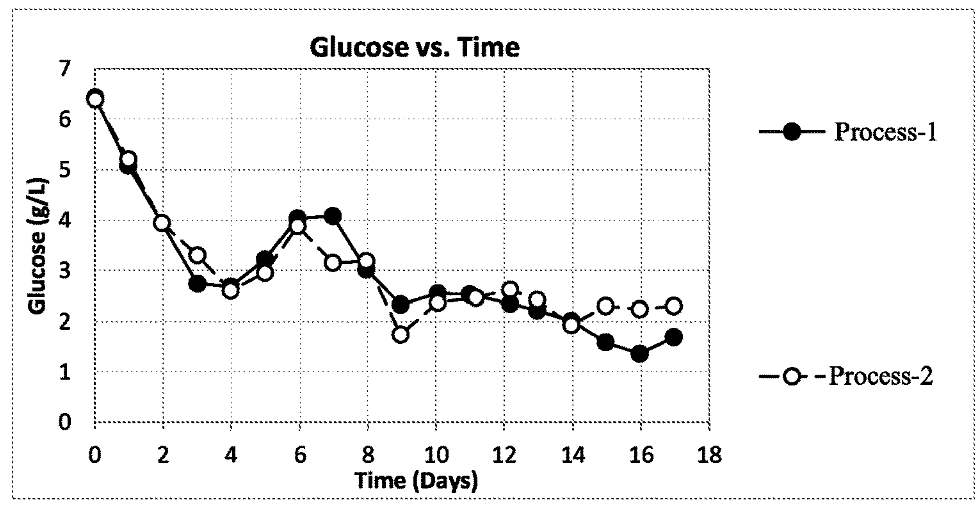
FIG. 5 showed the glucose concentration (g/L) in culture plotted versus the process time (days) for Process-1 and Process-2.

FIG. 5 showed that glucose concentrations in Process-1 and Process-2 were comparable.

Figure 6:
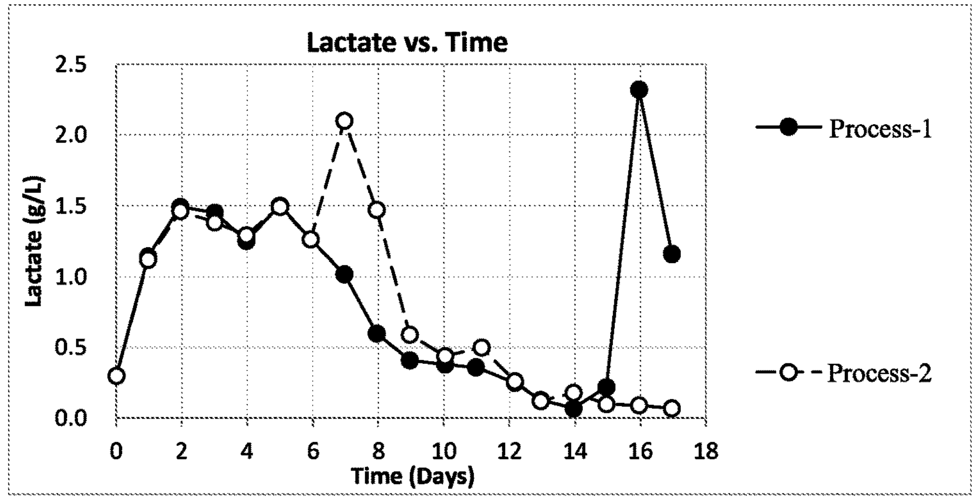
FIG. 6 showed the lactate concentration (g/L) in culture plotted versus the process time (days) for Process-1 and Process-2.

FIG. 6 showed that no obvious lactate production or accumulation problem was observed in either process.

Figure 7:
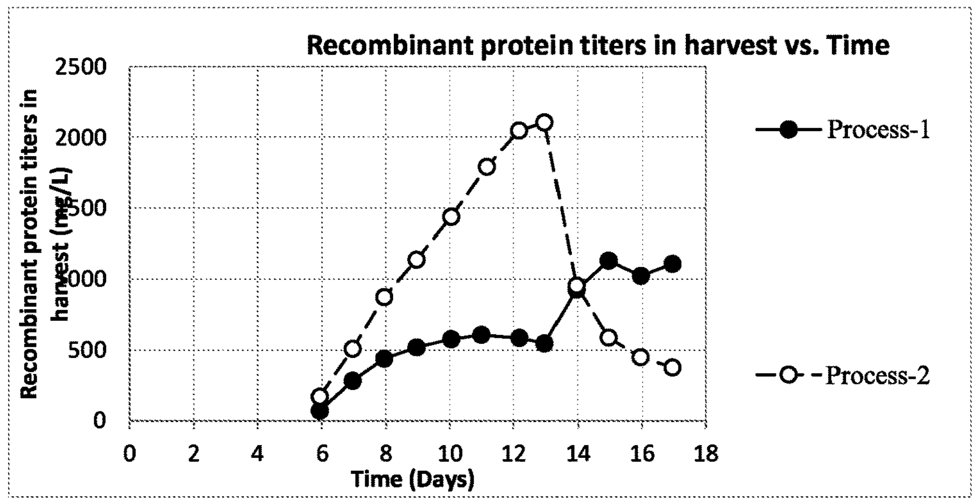
FIG. 7 showed the recombinant protein titer (g/L) in harvest plotted versus the process time (days) for Process-1 and Process-2.

FIG. 7 showed that the recombinant protein titer in harvest was significantly higher in the process with condensed harvest (in Process-1 after Day 13, and in Process-2 before Day 13).

Figure 8:
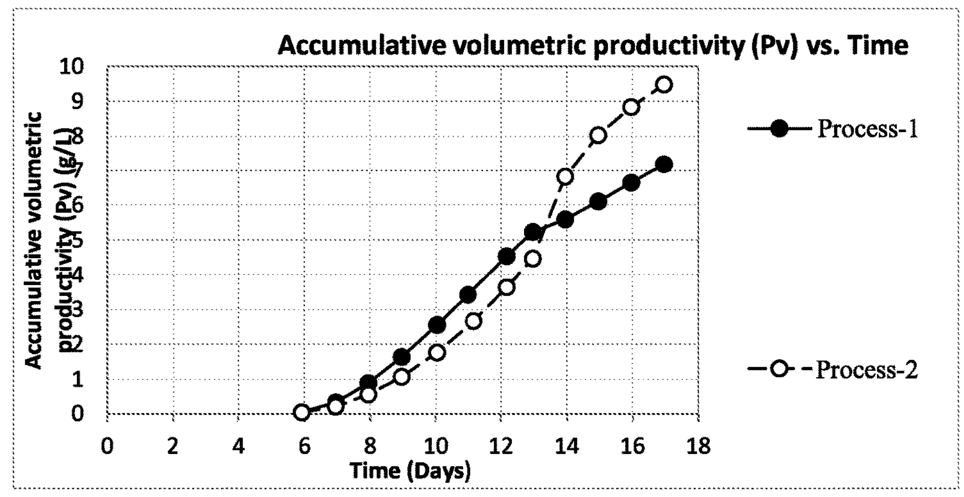
FIG. 8 showed the accumulative volumetric productivity (Pv) (g/L) plotted versus the process time (days) for Process-1 and Process-2.

FIG. 8 showed that accumulative volumetric productivity (Pv) was slightly lower in the process with condensed harvest (in Process-1 after Day 13, and in Process-2 before Day 13).

Figure 9:
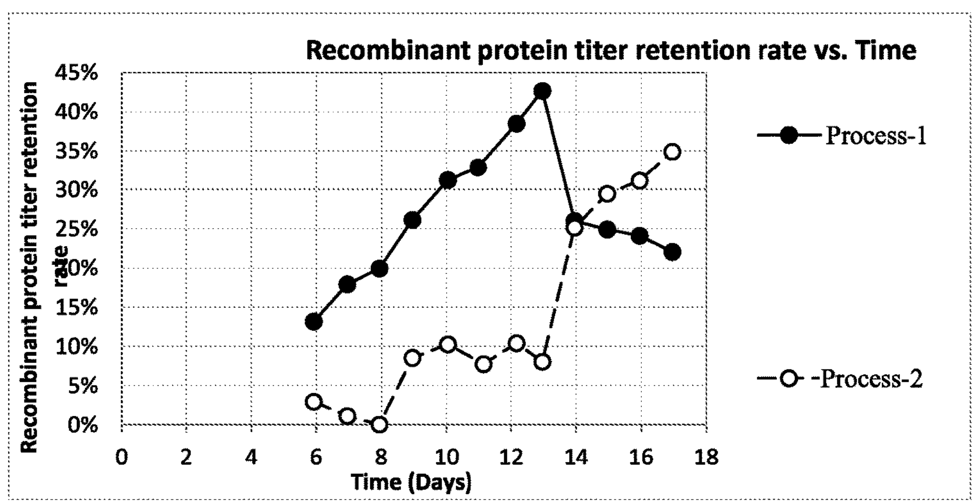
FIG. 9 showed the recombinant protein titer retention rate (%) plotted versus the process time (days) for Process-1 and Process-2.

FIG. 9 showed that the recombinant protein titer retention rate was remarkably lower in the process with condensed harvest (in Process-1 after Day 13, and in Process-2 before Day 13).

Example 2

In this example, using Clone X, the performance of an IPC process carried out with a prior art apparatus and method (Process A) and that of an IPC process carried out with the apparatus and method of the present disclosure were compared.

Process A:

Process A was performed in a 7 L Applikon vessel using delta V controller to control temperature at 36.5° C., a pH range of about between 7.2 and 6.8 and DO at 40% air saturation. A 0.2 μm cut-off hollow fiber filter (Spectrum labs) operated in ATF flow mode with an ATF-2H system (Refine Technology) was used to retain the cells.

The culture was started with an initial VCD of 0.90-1.10×$10^6$ cells/mL in CDM4 medium (Hyclone) supplemented with 4.0 mM L-Glutamine. About 10-100 ppm of antifoam was added every day from Day 0. Perfusion of basal medium (CDM4, Hyclone) was started from Day 1 at a rate of 0.4 VVD and increased to 1.0 VVD on Day 2 and kept until the end of culture. Perfusion of feed medium (CB7a/CB7b) was started from Day 3 at a rate of 2% of basal medium and gradually increased to 18% on Day 14 and maintained until Day 16. A microsparger was used to deliver oxygen when demanded. Temperature was shifted from 36.5° C. to 31.0° C. on Day 6 and kept at 31.0° C. until the end of culture.

The cell culture was continuously harvested through ATF. During the entire culture process, cells were retained in the bioreactor without bleeding.

Process B:

Process B was performed in a 3 L Applikon vessel using delta V controller to control temperature at 36.5° C., a pH range of about between 7.2 and 6.7 and DO at 40.0% air saturation. A 0.2 μm cut-off hollow fiber filter (filter 1) (Spectrum labs) operated in ATF flow mode with an ATF-2H system (Refine Technology) was used to retain the cells. A 50 kD (about 0.008 μm) cut-off hollow fiber filter (filter 2) (Spectrum labs) operated in ATF flow mode with an ATF-2H system (Refine Technology) was used to retain both cells and recombinant protein. The filter 1 and the filter 2 were fluidly connected to the Applikon vessel in a parallel manner via a branched pipe.

The culture was started with an initial VCD of 19.00-21.00×$10^6$ cells/mL in CDM4 medium (Hyclone) supplemented with 8.0 mM L-Glutamine. About 10-100 ppm of antifoam was added every day from Day 0. Perfusion of basal medium (CDM4, Hyclone) was started from Day 0 at a rate of 1.0 VVD and kept until the end of culture. Perfusion of feed medium (CB7a/CB7b) was started from Day 0 at a rate of 3% of basal medium and gradually increased to 8% on Day 6. From Day 9, it was gradually decreased to 6% on Day 12. Temperature was shifted from 36.5° C. to 31.0° C. on Day 2 and kept at 31.0° C. until the end of culture.

To perform a condensed continuous harvest, the filtrate through filter 1 with recombinant protein, namely the harvest, was continuously collected. Meanwhile, the filtrate through filter 2 without recombinant protein was discarded to keep a constant working volume. Harvest was started after temperature shift on Day 2 and the harvest rate was half of the perfusion rate thereafter. During the whole culture process, cells were retained in the bioreactor without bleeding.

Comparison Between the Process a and the Process B

The data for Process A were showed from Day 4 for a direct comparison of performance with Process B.

Figure 10:
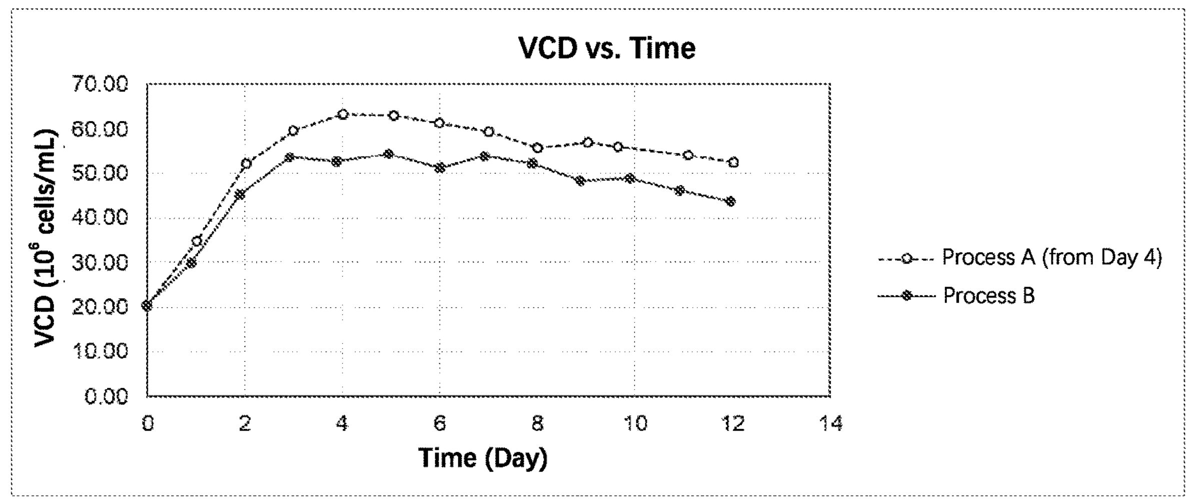
FIG. 10 compared the peak viable cell density achieved in both the Process A and the Process B.

FIG. 10 showed that a slightly higher peak viable cell density was achieved in the Process A.

Figure 11:
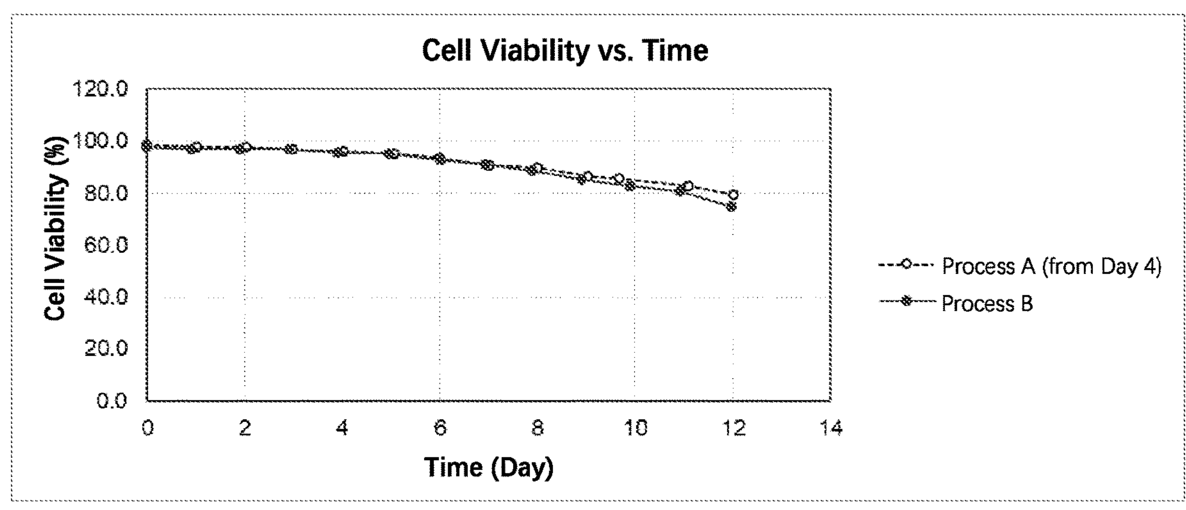
FIG. 11 compared the cell viability achieved in both the Process A and the Process B.

FIG. 11 showed that cell viability in both processes was comparable.

Figure 12:
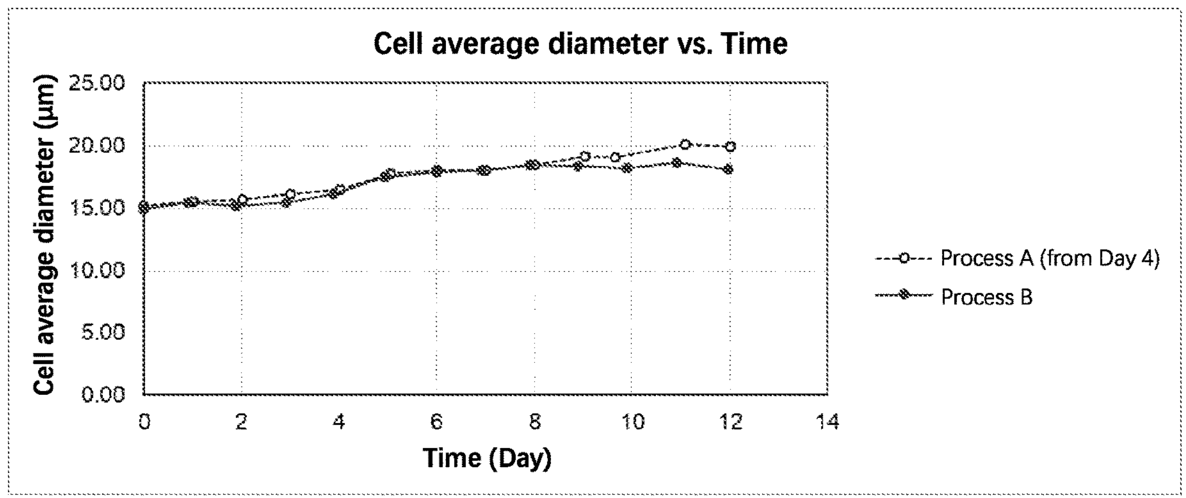
FIG. 12 compared the cell average diameters achieved in both the Process A and the Process B.

FIG. 12 showed that cell average diameters in both processes were comparable.

Figure 13:
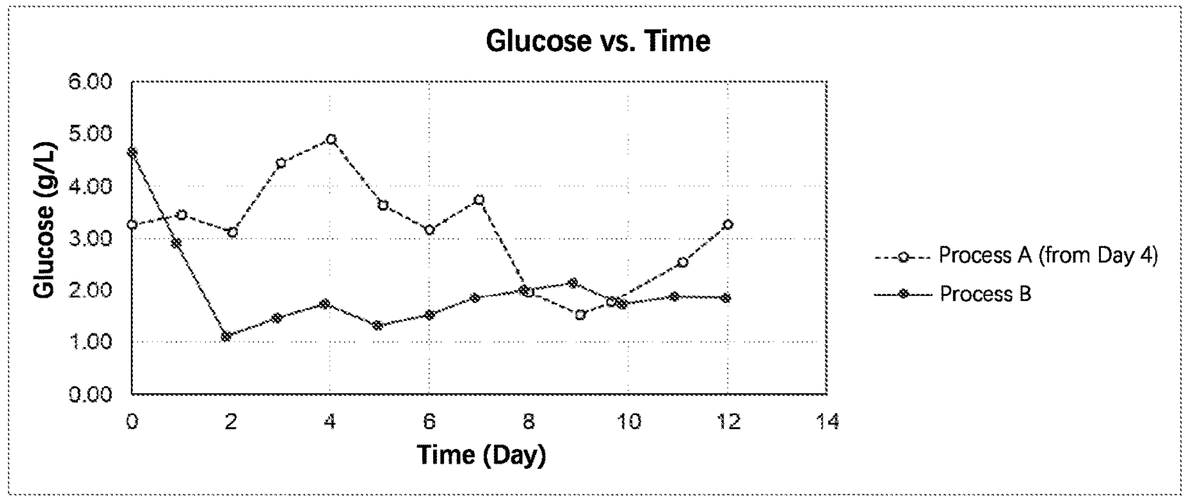
FIG. 13 compared the glucose concentrations in culture achieved in both the Process A and the Process B.

FIG. 13 showed that glucose concentrations in both processes were maintained above 1.00 g/L.

Figure 14:
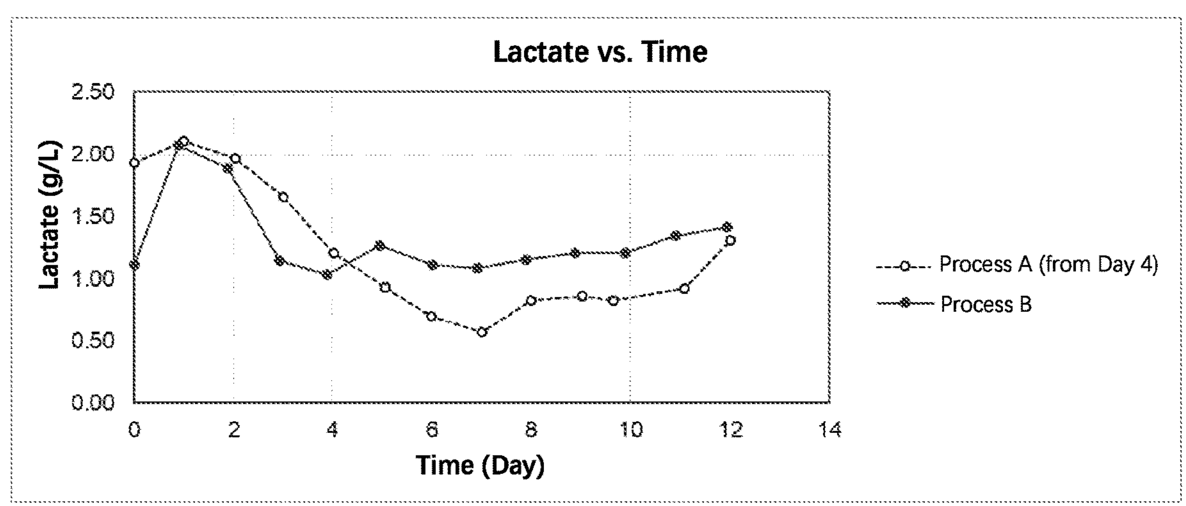
FIG. 14 compared the lactate concentrations in culture achieved in both the Process A and the Process B.

FIG. 14 showed that no obvious lactate production or accumulation problem was observed in either process.

Figure 15:
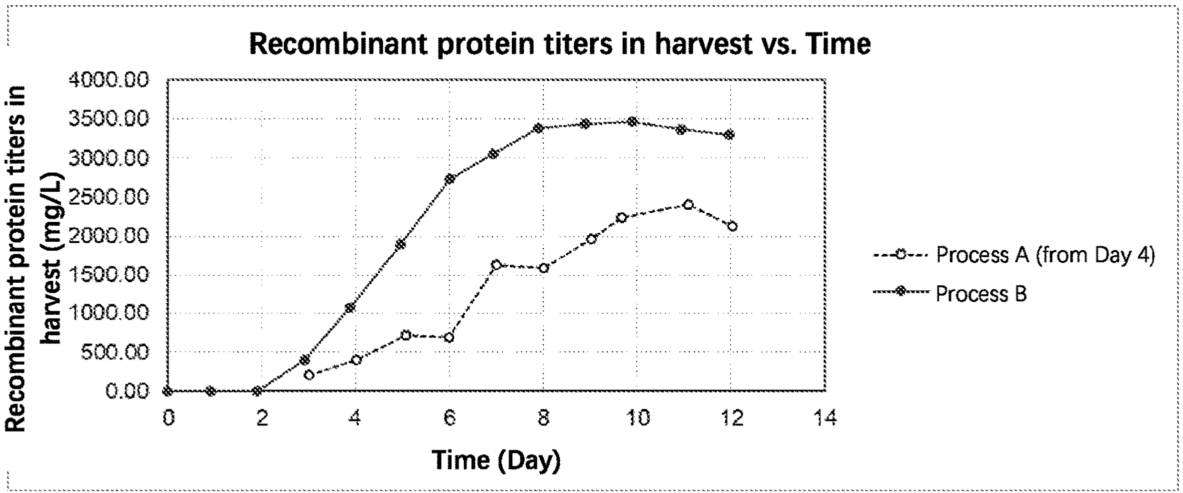
FIG. 15 compared the recombinant protein titers in harvest achieved in both the Process A and the Process B.

FIG. 15 showed that the recombinant protein titer in harvest was significantly higher in the Process B with the condensed harvest as compared to that in the Process A without the condensed harvest.

Figure 16:
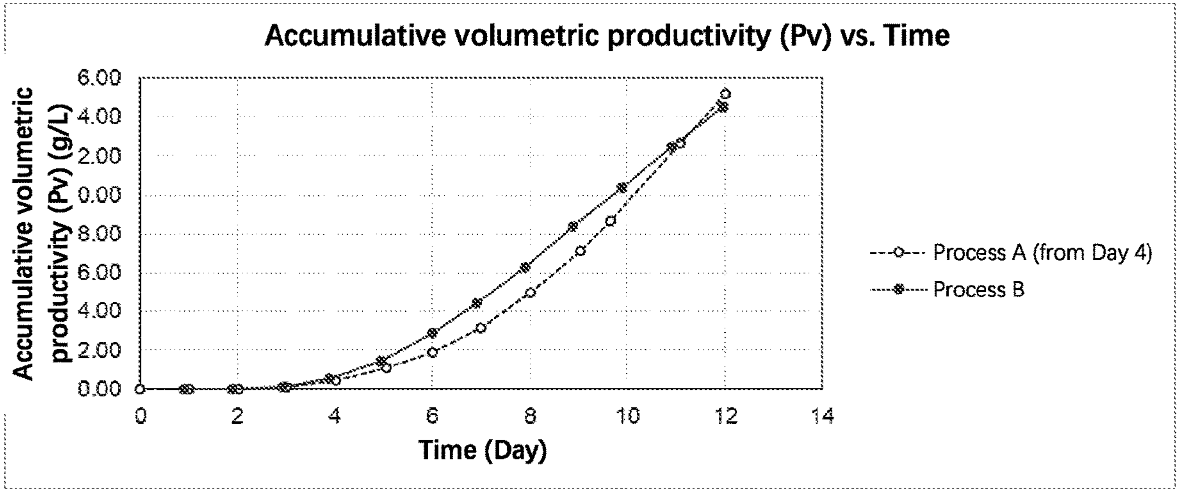
FIG. 16 compared the accumulative volumetric productivity (Pv) achieved in both the Process A and the Process B.

FIG. 16 showed that accumulative volumetric productivity (Pv) in both processes were comparable.

Figure 17:
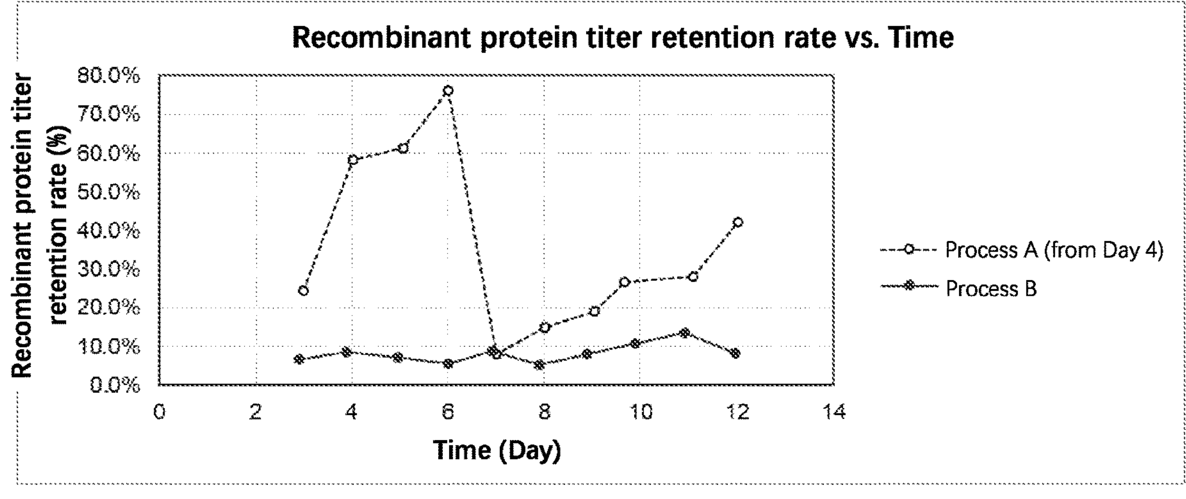
FIG. 17 compared the recombinant protein titer retention rates achieved in both the Process A and the Process B.

FIG. 17 showed that the recombinant protein titer retention rate was significantly lower in the Process B with the condensed harvest as compared to that in the Process A without the condensed harvest.

The invention claimed is:

1. An apparatus for continuously harvesting a biological substance produced by cultured cells, wherein the apparatus comprises:

(a) filter 1 which is at least one filter(s) having pore size(s) which do(es) not allow the cells to pass through the filter, but allow the biological substance to pass through the filter, (b) filter 2 which is at least one filter(s) having pore size(s) which do(es) not allow both the cells and the biological substance to pass through the filter, but keep fluid-flow-through of the filter, (c) a regulator that regulates the filtration rate of filter 1, and (d) a regulator that regulates the filtration rate of filter 2 wherein filter 1 and filter 2 are fluidly connected to an apparatus for culturing the cells in a parallel manner and wherein the (c) and (d) regulate the ratio of flow rate of cell culture through filter 1 and filter 2 to concentrate the biological substance first and then do not concentrate the biological substance in harvest liquid.

2. The apparatus of claim 1, wherein filter 1 and filter 2 are fluidly connected to the apparatus for culturing the cells (a) directly and separately, (b) via a branched pipe, or (c) a combination of (a) and (b).

3. The apparatus of claim 1, wherein filter 1 has a pore size of about 0.08 μm to 0.5 μm.

4. The apparatus of claim 1, wherein filter 2 has a molecular weight cut-off (MWCO) of 50 kD or less.

5. The apparatus of claim 1, wherein either or both of filter 1 and filter 2 is/are alternating tangential flow (ATF) filter(s) or tangential flow filtration (TFF) filter(s).

6. The apparatus of claim 5, wherein either or both of filter 1 and the filter 2 is/are hollow fiber filter(s).

7. The apparatus of claim 1, wherein, the number of filter(s) in filter 1 is 1, 2, 3 or more, and/or the number of filter(s) in filter 2 is 1, 2, 3 or more.

8. The apparatus of claim 1, wherein filter 1 has a pore size of about 0.1 μm to 0.4 μm.

9. The apparatus of claim 1, wherein filter 1 has a pore size of about 0.2 μm.

10. A system for producing a biological substance, wherein the system comprises:

(a) a cell culture apparatus with a basal medium and a feed medium in a perfusion manner; and (b) the apparatus of claim 1.

11. The system of claim 10 further comprising a biological substance capturer.

12. The system of claim 10 further comprising a microsparger.

13. A method for continuously harvesting a biological substance produced by cultured cells, comprising:

continuously harvesting a biological substance produced by cells cultured in an apparatus for culturing the cells with a basal medium and a feed medium in a perfusion manner with an apparatus comprising:

(a) filter 1 which is at least one filter(s) having pore size(s) which do(es) not allow the cells to pass through the filter, but allow the biological substance to pass through the filter, and (b) filter 2 which is at least one filter(s) having pore size(s) which do(es) not allow both the cells and the biological substance to pass through the filter, but keep fluid-flow-through of the filter; and (c) a regulator that regulates the filtration rate of filter 1, and (d) a regulator that regulates the filtration rate of filter 2, wherein filter 1 and filter 2 are fluidly connected to the apparatus for culturing the cells in a parallel manner, and wherein the (c) and (d) regulate the ratio of flow rate of cell culture through filter 1 and filter 2 to concentrate the biological substance first and then do not concentrate the biological substance in harvest liquid.

14. The method of claim 13, wherein the cells comprise mammalian cells.

15. The method of claim 14, wherein the mammalian cells comprise CHO (Chinese Hamster Ovary) cells, hybridomas, BHK (Baby Hamster Kidney) cells, or myeloma cells.

16. The method of claim 13, wherein the biological substance is chosen from receptors, enzymes, fusion proteins, blood proteins, multifunctional proteins, viral or bacterial proteins, and immunoglobulins.

17. The method of claim 16, wherein said blood proteins are from the blood coagulation cascade.

18. The method of claim 16, wherein said multifunctional proteins are erythropoietin.

19. The method of claim 16, wherein said viral or bacterial proteins are used in vaccines.

20. The method of claim 16, wherein said immunoglobulins are antibodies or multi-specific antibodies.

21. The method of claim 20, wherein said antibodies are IgG or IgM.

22. The method of claim 20, wherein said multi-specific antibodies are bi-specific antibodies.

23. A method for producing a biological substance, comprising:

culturing cells in an apparatus for culturing the cells with a basal medium and a feed medium in a perfusion manner; and continuously harvesting a biological substance produced by the cultured cells with an apparatus comprising:

(a) filter 1 which is at least one filter(s) having pore size(s) which do(es) not allow the cells to pass through the filter, but allow the biological substance to pass through the filter, and (b) filter 2 which is at least one filter(s) having pore size(s) which do(es) not allow both the cells and the biological substance to pass through the filter, but keep fluid-flow-through of the filter; and (c) a regulator that regulates the filtration rate of filter 1, and (d) a regulator that regulates the filtration rate of filter 2, wherein filter 1 and filter 2 are fluidly connected to the apparatus for culturing the cells in a parallel manner, and wherein the (c) and (d) regulate the ratio of flow rate of cell culture through filter 1 and filter 2 to concentrate the biological substance first and then do not concentrate the biological substance in harvest liquid.

* * * * *